(12) United States Patent
Huang et al.

(10) Patent No.: US 12,263,345 B2
(45) Date of Patent: Apr. 1, 2025

(54) ELECTRONIC DEVICE AND METHOD FOR DETERMINING INTENSITY OF LOW-FREQUENCY CURRENT

(71) Applicant: Acer Incorporated, New Taipei (TW)

(72) Inventors: Yi-Jin Huang, New Taipei (TW); Yin-Hsong Hsu, New Taipei (TW); Wei-Hao Chang, New Taipei (TW); Chien-Hung Li, New Taipei (TW)

(73) Assignee: Acer Incorporated, New Taipei (TW)

( * ) Notice: Subject to any disclaimer, the term of this patent is extended or adjusted under 35 U.S.C. 154(b) by 1009 days.

(21) Appl. No.: 17/243,539

(22) Filed: Apr. 28, 2021

(65) Prior Publication Data

US 2022/0296905 A1    Sep. 22, 2022

(30) Foreign Application Priority Data

Mar. 18, 2021    (TW) .................. 110109782

(51) Int. Cl.
*A61N 1/36*    (2006.01)
*A61B 5/395*    (2021.01)
*A61B 5/397*    (2021.01)

(52) U.S. Cl.
CPC .......... *A61N 1/36171* (2013.01); *A61B 5/395* (2021.01); *A61B 5/397* (2021.01); *A61N 1/36139* (2013.01)

(58) Field of Classification Search
None
See application file for complete search history.

(56) References Cited

U.S. PATENT DOCUMENTS

| 11,744,482 B1 * | 9/2023 | Giuffrida ............... G16H 50/20 |
| | | 607/45 |
| 2014/0148725 A1 | 5/2014 | Cadwell |
| 2016/0144172 A1 * | 5/2016 | Hsueh ................... A61B 5/389 |
| | | 607/48 |
| 2018/0304075 A1 | 10/2018 | Su et al. |
| 2019/0370636 A1 * | 12/2019 | Isopoussu ........... H04B 1/0003 |

(Continued)

FOREIGN PATENT DOCUMENTS

| CN | 102886102 | 1/2013 |
| CN | 209392593 | 9/2019 |

(Continued)

OTHER PUBLICATIONS

"Search Report of Europe Counterpart Application", issued on Oct. 8, 2021, p. 1-p. 7.

*Primary Examiner* — Erica S Lee
(74) *Attorney, Agent, or Firm* — JCIPRNET

(57) ABSTRACT

An electronic device and a method for determining the intensity of a low-frequency current are provided. The method includes: individually applying a corresponding first current to a body part of a user in N consecutive time intervals, wherein the time intervals include an i-th time interval to an (i+N)-th time interval; obtaining electromyography values of the body part in each time interval; determining a second current corresponding to an (i+N+1)-th time interval based on the first current corresponding to each time interval, the body part, personal information of the user, and the electromyography values of each time interval; and applying a second current to the body part of the user in the (i+N+1)-th time interval.

9 Claims, 4 Drawing Sheets

(56) References Cited

U.S. PATENT DOCUMENTS

2020/0139115 A1\* 5/2020 Verity ................ A61N 1/36003
2020/0139123 A1\* 5/2020 Samejima .......... A61N 1/36034

FOREIGN PATENT DOCUMENTS

| | | |
|---|---:|---:|
| CN | 110464347 | 11/2019 |
| DE | 10261261 | 7/2004 |
| EP | 2522274 | 11/2012 |
| TW | 201641128 | 12/2016 |
| TW | 201811288 | 4/2018 |
| WO | 2020183356 | 9/2020 |

\* cited by examiner

ELECTRONIC DEVICE AND METHOD FOR DETERMINING INTENSITY OF LOW-FREQUENCY CURRENT

CROSS-REFERENCE TO RELATED APPLICATION

This application claims the priority benefit of Taiwan application serial no. 110109782, filed on Mar. 18, 2021. The entirety of the above-mentioned patent application is hereby incorporated by reference herein and made a part of this specification.

BACKGROUND

Technical Field

The disclosure relates to a technique for determining the current intensity, and in particular to a method for determining the intensity of a low-frequency current and an electronic device.

Description of Related Art

In rehabilitation departments or relevant medical places, electrotherapy of patients through electrotherapy instrument has become a very common medical treatment. In addition, there are also various low-frequency electrotherapy instrument on the market for the user to perform electrotherapy on their own according to requirements after purchase.

In the medical places, most of the electrotherapy instrument are controlled by relevant medical personnel. However, the user must control the current intensity of the low-frequency electrotherapy instrument on their own when using the low-frequency electrotherapy instrument on their own. Generally speaking, the medical effects provided by the low-frequency electrotherapy instrument are not directly related to the current intensity thereof, and an excessive current intensity may sometimes cause harm to the user.

Therefore, for persons skilled in the art, how to design a mechanism for automatically determining the intensity of a low-frequency current is indeed an important topic.

SUMMARY

The disclosure provides a method for determining the intensity of a low-frequency current and an electronic device, which can be used to solve the above technical issue.

The disclosure provides a method for determining the intensity of a low-frequency current, which is applicable to an electronic device and includes the following steps. A corresponding first current is individually applied to a body part of a user through an electrode patch in N consecutive time intervals. The time intervals include an i-th time interval to an (i+N)-th time interval, where i and N are positive integers. Multiple electromyography values of the body part in each time interval are obtained through an electromyography value measurement circuit. A second current corresponding to an (i+N+1)-th time interval is determined based on the first current corresponding to each time interval, the body part, at least one personal information of the user, and the electromyography values of each time interval. The second current is applied to the body part of the user through the electrode patch in the (i+N+1)-th time interval.

The disclosure provides an electronic device, which includes an electromyography value measurement circuit, a storage circuit, an electrode patch, and a processor. The storage circuit stores a code. The processor is coupled to the electromyography value measurement circuit, the storage circuit, and the electrode patch, and accesses the code to execute the following steps. A corresponding first current is individually applied to a body part of a user through an electrode patch in N consecutive time intervals. The time intervals include an i-th time interval to an (i+N)-th time interval, where i and N are positive integers. Multiple electromyography values of the body part in each time interval are obtained through an electromyography value measurement circuit. A second current corresponding to an (i+N+1)-th time interval is determined based on the first current corresponding to each time interval, the body part, at least one personal information of the user, and the electromyography values of each time interval. The second current is applied to the body part of the user through the electrode patch in the (i+N+1)-th time interval.

DETAILED DESCRIPTION OF DISCLOSED EMBODIMENTS

Figure 1:
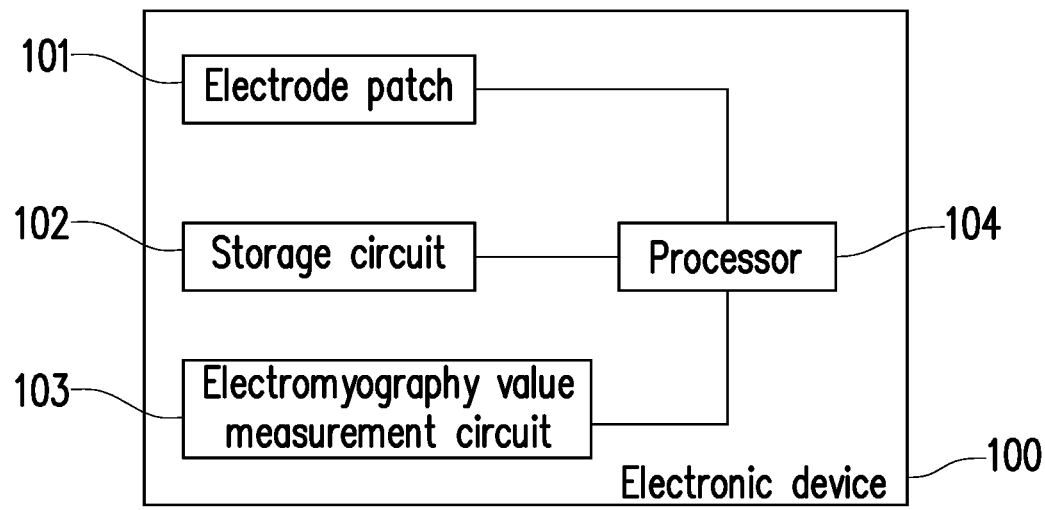
FIG. 1 is a schematic diagram of an electronic device according to an embodiment of the disclosure.

Please refer to FIG. 1, which is a schematic diagram of an electronic device according to an embodiment of the disclosure. In different embodiments, an electronic device 100 is, for example, a portable low-frequency therapy instrument or other similar devices/instruments, but not limited thereto.

As shown in FIG. 1, the electronic device 100 includes an electrode patch 101, a storage circuit 102, an electromyography value measurement circuit 103, and a processor 104. In the embodiment of the disclosure, the electrode patch 101 may be, for example, attached to a body part of a user who intends to undergo electrotherapy, and the processor 104 may be used to determine a current to be applied to the body part through the electrode patch 101, but not limited thereto. The electromyography value measurement circuit 103 may, for example, have a corresponding electrode patch (for example, the electrode patch 101 or other additional electrode patches), and the electrode patch may be attached to the body part to measure electromyography values of the body part, but not limited thereto.

The storage circuit 102 is, for example, any type of fixed or removable random access memory (RAM), read-only memory (ROM), flash memory, hard disk, other similar devices, or a combination of these devices that may be used to record multiple codes or modules.

The processor 104 is coupled to the storage circuit 102 and may be a general-purpose processor, a specific-purpose processor, a traditional processor, a digital signal processor, multiple microprocessors, one or more microprocessors combined with a digital signal processor core, controllers, microcontrollers, application specific integrated circuits (ASIC), field programmable gate array (FPGA), any other types of integrated circuits, state machines, advanced reduced instruction set computer (RISC) machine (ARM) processors, and similar products.

In the embodiment of the disclosure, the processor 104 may access modules and codes recorded in the storage circuit 102 to implement the method for determining the intensity of a low-frequency current proposed by the disclosure. The details thereof are as follows.

Figure 2:
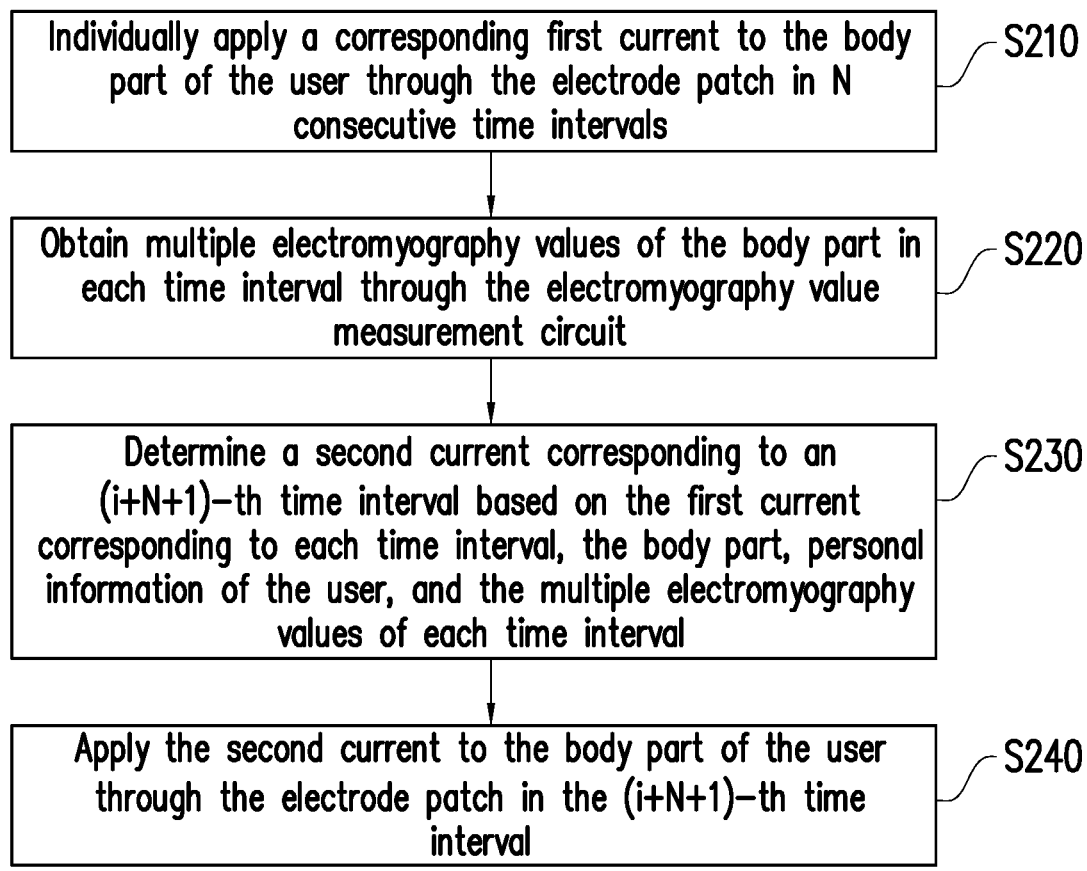
FIG. 2 is a flowchart of a method for determining the intensity of a low-frequency current according to an embodiment of the disclosure.

Please refer to FIG. 2, which is a flowchart of a method for determining the intensity of a low-frequency current according to an embodiment of the disclosure. The method of this embodiment may be executed by the electronic device 100 of FIG. 1. The details of each step in FIG. 2 will be described below in conjunction with the elements shown in FIG. 1.

First, in Step S210, the processor 104 may individually apply a corresponding first current to the body part of the user through the electrode patch 101 in N consecutive time intervals. Next, in Step S220, the processor 104 may obtain multiple electromyography values of the body part in each time interval through the electromyography value measurement circuit 103. For ease of understanding the concept of the disclosure, the following will be further described with reference to FIG. 3.

Figure 3:
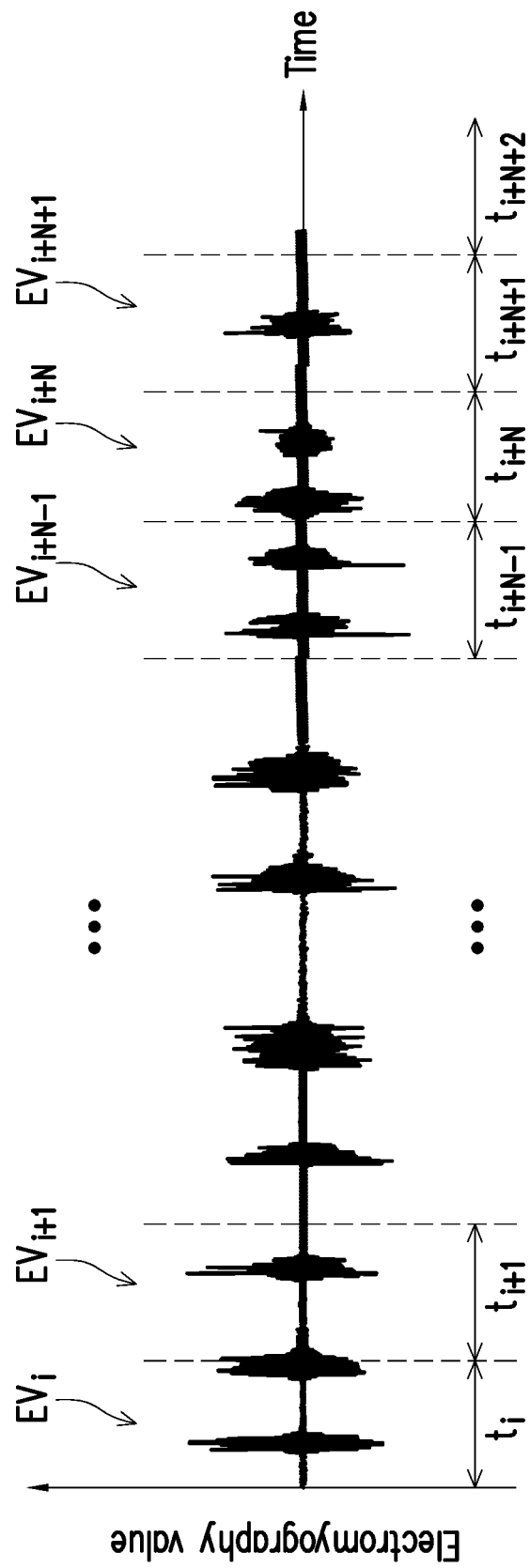
FIG. 3 is a waveform diagram of electromyography values according to an embodiment of the disclosure.

Please refer to FIG. 3, which is a waveform diagram of electromyography values according to an embodiment of the disclosure. In FIG. 3, it is assumed that the processor 104 individually applies the corresponding first current to the body part of the user through the electrode patch 101 in N consecutive time intervals $t_i$ to $t_{i+N}$ (that is, an i-th time interval to an (i+N)-th time interval), and the processor 104 obtains the electromyography values of the body part in each time interval through the electromyography value measurement circuit 103.

In the embodiment of the disclosure, the electromyography values measured in the time interval $t_i$ may be, for example, integratedly expressed as an electromyography value $EV_i$, and the electromyography values measured in the time interval $t_{i+1}$ may be, for example, integratedly expressed as an electromyography value $EV_{i+1}$. Accordingly, the meaning of the electromyography values $EV_{i+N-1}$ to $EV_{i+N+1}$ corresponding to the time intervals $t_{i+N-1}$ to $t_{i+N+1}$ may be deduced by analogy, which will not be repeated.

Then, in Step S230, the processor 104 may determine a second current corresponding to an (i+N+1)-th time interval (that is, the time interval $t_{i+N+1}$) based on the first current corresponding to each time interval $t_i$ to $t_{i+N}$, the body part, personal information of the user, and the multiple electromyography values $EV_i$ to $EV_{i+N}$ of each time interval $t_i$ to $t_{i+N}$. For ease of understanding, the details of Step S230 will be described below with reference to FIG. 4.

Figure 4:
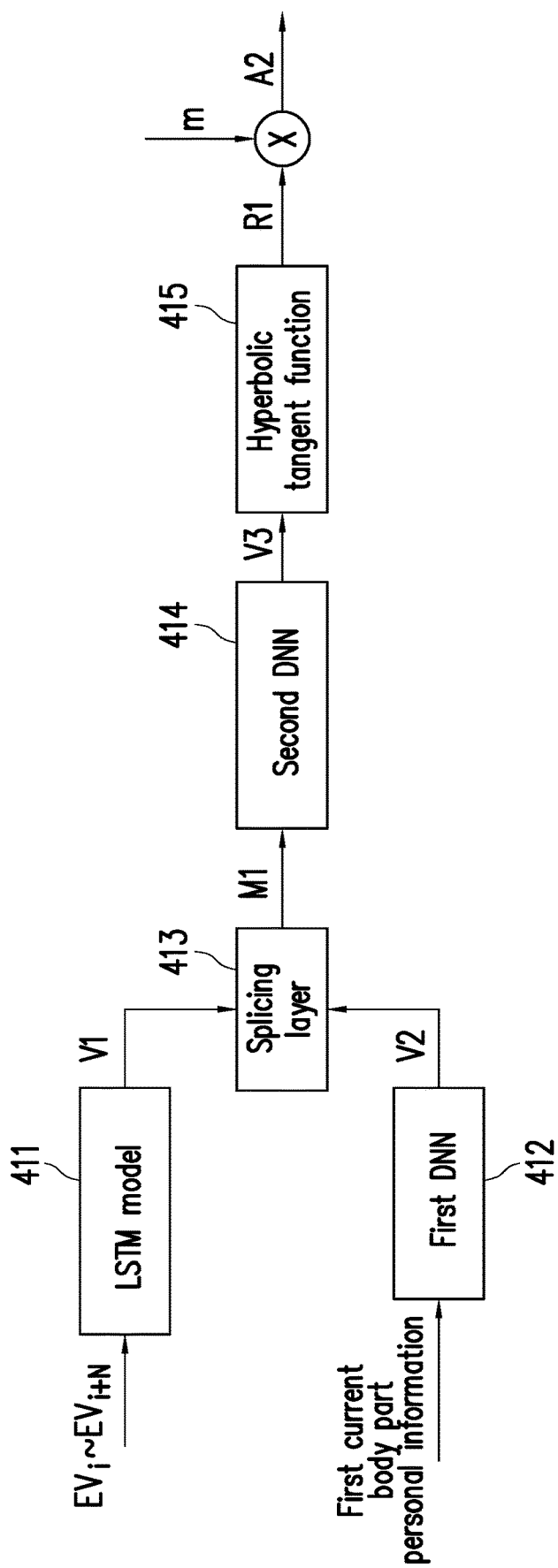
FIG. 4 is a schematic diagram of determining a second current corresponding to an (i+N+1)-th time interval according to FIG. 3.

Please refer to FIG. 4, which is a schematic diagram of determining a second current corresponding to an (i+N+1)-th time interval according to FIG. 3. In an embodiment, the processor 104 may convert the multiple electromyography values $EV_i$ to $EV_{i+N}$ in each time interval $t_i$ to $t_{i+N}$ into a first vector V1. In FIG. 4, the processor 104 may, for example, first obtain a long short term memory (LSTM) model 411 including a 1-st hidden layer to an N-th hidden layer connected in series. After that, the processor 104 may respectively input the electromyography values $EV_i$ to $EV_{i+N}$ into the 1-st hidden layer to the N-th hidden layer.

Correspondingly, the LSTM model 411 may generate the first vector V1 in response to the electromyography values $EV_i$ to $EV_{i+N}$, so as to characterize the correlation between the electromyography values $EV_i$ to $EV_{i+N}$, but not limited thereto.

In addition, the processor 104 may convert the first current corresponding to each time interval, the body part, and the personal information (for example, gender, age, etc.) of the user into a second vector V2, and splice the first vector V1 and the second vector V2 into a specific matrix M1.

In FIG. 4, the processor 104 may, for example, input the first current corresponding to each time interval, the body part, and the personal information of the user into a first deep neural network (DNN) 412. The first DNN 412 may generate the second vector V2 in response to the first current corresponding to each time interval, the body part, and the personal information of the user, but not limited thereto. After that, the processor 104 may splice the first vector V1 and the second vector V2 into the specific matrix M1 in a left-right or up-down splicing manner through a splicing layer 413, but not limited thereto.

Then, the processor 104 may convert the specific matrix M1 into a third vector V3, and convert the third vector V3 into a reference coefficient R1. In FIG. 4, the processor 104 may, for example, input the specific matrix M1 into a second DNN 414. The second DNN 414 may generate the third vector V3 in response to the specific matrix M1, but not limited thereto. In addition, the processor 104 may, for example, input the third vector V3 into a hyperbolic tangent function 415 to convert the third vector V3 into the reference coefficient R1 between −1 and 1, but not limited thereto.

After that, the processor 104 may multiply the reference coefficient R1 by a constant m to generate a second current A2 corresponding to the time interval $t_{i+N+1}$.

In Step S240, the processor 104 may apply the second current A2 to the body part of the user through the electrode patch 101 in the (i+N+1)-th time interval. In this way, the method of the disclosure may more appropriately determine the second current A2 corresponding to the time interval $t_{i+N+1}$ after comprehensively considering the electromyography values in the past N time intervals $t_i$ to $t_{i+N}$, the first current corresponding to each time interval $t_i$ to $t_{i+N}$, the personal information of the user, and the body part attached to the electrode patch 101.

In addition, for the (i+N+2)-th time interval (that is, the time interval $t_{i+N+2}$), the processor 104 may still execute a mechanism similar to the above teaching to determine the third current corresponding to the time interval $t_{i+N+2}$.

Roughly speaking, the processor 104 may obtain the electromyography value $EV_{i+N+1}$ of the body part in the time interval $t_{i+N+1}$ through the electromyography value measurement circuit 103; determine the third current corresponding to the time interval $t_{i+N+2}$ based on the second current A2, the body part, the personal information of the user, and the electromyography values $EV_{i+1}$ to $EV_{i+N+1}$; and apply the third current to the body part of the user through the electrode patch 101 in the time interval $t_{i+N+2}$. For the details of the above steps, please refer to the relevant descriptions in FIG. 2 to FIG. 4, which will not be repeated.

It can be seen from the above that the disclosure may determine the current used by the next time interval after comprehensively considering the electromyography values in the past N time intervals, the current corresponding to each time interval, the personal information of the user, and the body part attached to the electrode patch 101, thereby achieving the effect of intelligently adjusting the current intensity used during low-frequency therapy. In this way, poor therapeutic effect due to the user improperly selecting the current intensity may be prevented.

In some embodiments, in addition to the current intensity applied to the body part, the time length of the overall therapy is also a very important factor. The therapeutic effect is correspondingly reduced due to the therapy time being too long or too short. Therefore, the disclosure also proposes the following mechanism, which may be used to determine when to stop applying a current to the body part of the user, as detailed below.

Figure 5:
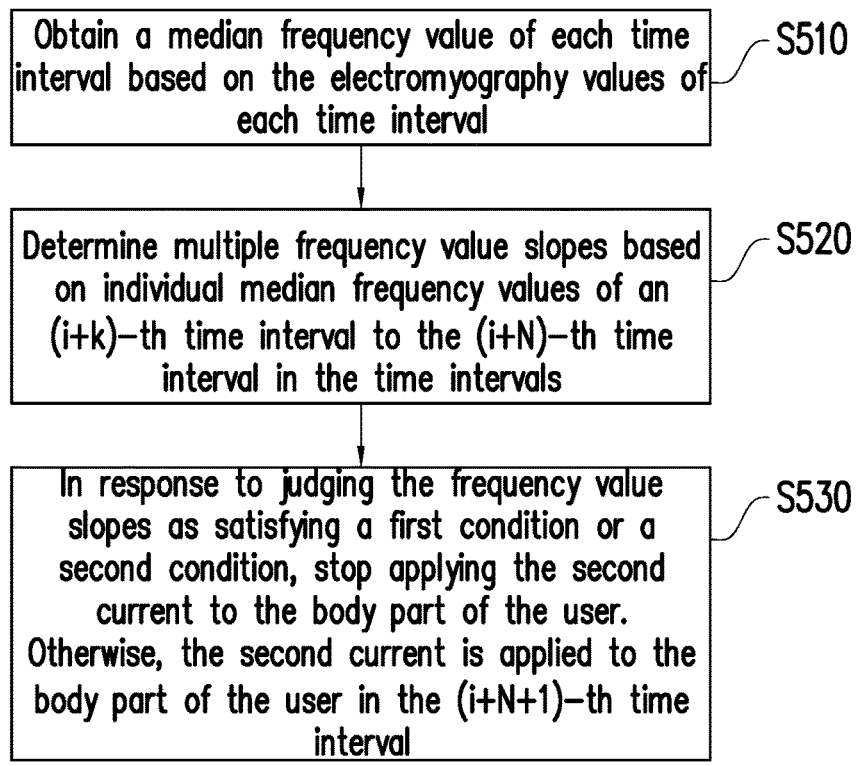
FIG. 5 is a flowchart of a mechanism of judging to stop applying a current according to an embodiment of the disclosure.
Figure 6:
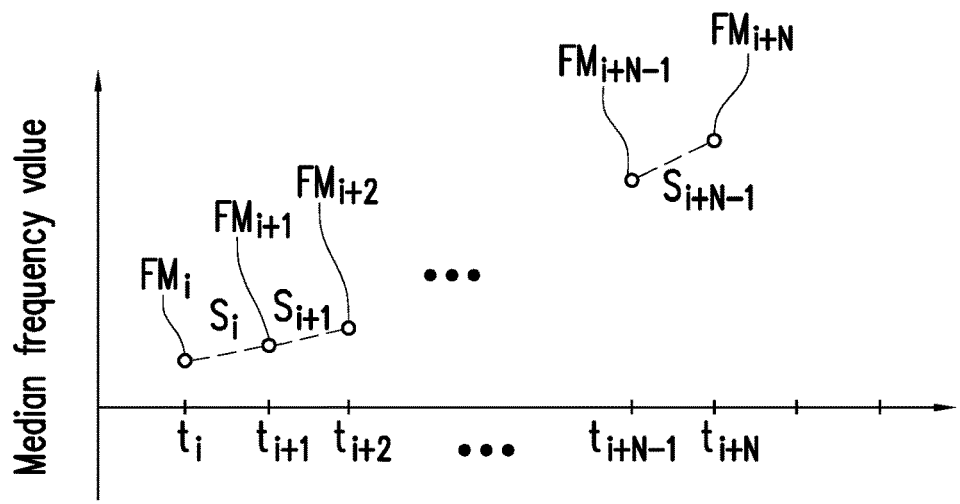
FIG. 6 is a schematic diagram of median frequency values according to FIG. 3.

Please refer to FIG. 5, which is a flowchart of a mechanism of judging to stop applying a current according to an embodiment of the disclosure. The method of this embodiment may be executed by the electronic device 100 of FIG. 1. The details of each step of FIG. 5 will be described below in conjunction with the elements shown in FIG. 1. In addition, for ease of understanding the concept of the disclosure, the following will be described with reference to the scenarios of FIG. 3 and FIG. 6. FIG. 6 is a schematic diagram of median frequency values according to FIG. 3.

Generally speaking, before executing Step S240 of FIG. 2, the processor 104 may first execute each step in FIG. 5 to determine whether to continue applying the second current A2 in the time interval $t_{i+N+1}$.

First, in Step S510, the processor 104 may obtain a median frequency value of each time interval $t_i$ to $t_{i+N}$ based on the electromyography values $EV_i$ to $EV_{i+N}$ of each time interval $t_i$ to $t_{i+N}$. Taking the time interval $t_i$ as an example, the processor 104 may perform computations such as the Fourier transformation and normalization integration on the electromyography value $EV_i$ to estimate a median frequency value $FM_i$ corresponding to the time interval $t_i$. Taking the time interval $t_{i+1}$ as another example, the processor 104 may perform computations such as the Fourier transform and normalization integration on the electromyography value $EV_{i+1}$ to estimate a median frequency value $FM_{i+1}$ corresponding to the time interval $t_{i+1}$. For other time intervals (for example, the time intervals $t_{i+N-1}$ and $t_{i+N}$), the processor 104 may estimate the corresponding median frequency value (for example, median frequency values $FM_{i+N-1}$ and $FM_{i+N}$) based on a similar mechanism, but not limited thereto.

After that, in Step S520, the processor 104 may determine multiple frequency value slopes based on individual median frequency values of an (i+k)-th time interval (that is, the time interval $t_{i+k}$) to the (i+N)-th time interval in the time intervals $t_i$ to $t_{i+N}$, where k≤N−1. In different embodiments, the designer may determine the value of k according to requirements. In the following descriptions, k is exemplified as 0, but not limited thereto.

When k is 0, the processor 104 may determine multiple frequency value slopes based on individual median frequency values of the time intervals $t_i$ to $t_{i+N}$. In FIG. 6, the processor 104 may estimate the slope between the median frequency values $FM_i$ and $FM_{i+1}$ as a frequency value slope $S_i$. Similarly, the processor 104 may estimate the slope between the median frequency values $FM_{i+1}$ and $FM_{i+2}$ as a frequency value slope $S_{i+1}$. Based on this principle, the processor 104 may determine frequency value slopes $S_i$ to $S_{i+N-1}$ based on the individual median frequency values of the time intervals $t_i$ to $t_{i+N}$.

After that, in Step S530, in response to judging the frequency value slopes $S_i$ to $S_{i+N-1}$ as satisfying a first condition or a second condition, the processor 104 may stop applying the second current A2 to the body part of the user.

Otherwise, the second current A2 may be applied to the body part of the user in the time interval $t_{i+N+1}$ through the electrode patch 101.

In an embodiment, in response to judging n consecutive frequency value slopes $S_i$ to $S_{i+N-1}$ (n may be determined by the designer according to requirements) as all positive and individual absolute values thereof as all less than a first preset value (for example, 0.1), the processor 104 may judge that the frequency value slopes $S_i$ to $S_{i+N-1}$ satisfy the first condition. Otherwise, the frequency value slopes $S_i$ to $S_{i+N-1}$ are judged as not satisfying the first condition.

Specifically, the median frequency values $FM_i$ to $FM_{i+N}$ corresponding to the time intervals $t_i$ to $t_{i+N}$, may be respectively used to characterize indicators of muscle states in each time interval $t_i$ to $t_{i+N}$. A lower median frequency value represents that the muscles of the body part are in a fatigue or tight state, while a higher median frequency value represents that the muscles of the body part are in a non-fatigue or relaxed state.

When the processor 104 judges that the n consecutive frequency value slopes $S_i$ to $S_{i+N-1}$ are all positive and the individual absolute values thereof are all less than the first preset value (for example, 0.1), it represents that the body part of the user is gradually relaxed, so it can be known that a certain degree of therapeutic effect has been obtained. Therefore, the processor 104 may correspondingly stop applying the second current A2 to stop continuing to treat the body part of the user. On the other hand, when the processor 104 judges that the frequency value slopes $S_i$ to $S_{i+N-1}$ do not satisfy the first condition, it represents that the body part of the user may need further therapy, so the processor 104 may correspondingly execute Step S240, but not limited thereto.

In an embodiment, in response to judging the n consecutive frequency value slopes $S_i$ to $S_{i+N-1}$ as all negative or the individual absolute values thereof as all greater than a second preset value (for example, 0.6), the processor 104 may judge that the frequency value slopes $S_i$ to $S_{i+N-1}$ satisfy the second condition. Otherwise, the frequency value slopes $S_i$ to $S_{i+N-1}$ may be judged as not satisfying the second condition.

Specifically, when the processor 104 judges that the n consecutive frequency value slopes $S_i$ to $S_{i+N-1}$ are all negative or the individual absolute values thereof are all greater than the second preset value, it represents that the body part of the user has not obtained the therapeutic effect, but shows worsening conditions such as more tightness and fatigue. Therefore, the processor 104 may correspondingly stop applying the second current A2 to stop continuing to treat the body part of the user. On the other hand, when the processor 104 judges that the frequency value slopes $S_i$ to $S_{i+N-1}$ do not satisfy the second condition, it represents that the body part of the user may still undergo further therapy, so the processor 104 may correspondingly execute Step S240, but not limited thereto.

It can be seen from the above that the disclosure may appropriately determine when to stop applying a current to the user, thereby preventing the user from being unable to obtain a better therapeutic effect due to the therapy time being too long or too short.

In summary, the disclosure may determine the current used by the next time interval after comprehensively considering the electromyography values in the past N time intervals, the current corresponding to each time interval, the personal information of the user, and the body part, thereby achieving the effect of intelligently adjusting the current intensity used during low-frequency therapy. In this way, poor therapeutic effect due to the user improperly selecting the current intensity may be prevented.

In addition, the disclosure may also determine whether the body part of the user has obtained a certain degree of therapeutic effect or has worsened according to the changing condition of the median frequency values corresponding to each time interval. When it is judged that the body part of the user has obtained good therapy or has worsened, the disclosure may stop the therapy in time to prevent the user from being unable to obtain a better therapeutic effect due to the therapy time being too long or too short.

Although the disclosure has been disclosed in the above embodiments, the embodiments are not intended to limit the disclosure. Persons skilled in the art may make some changes and modifications without departing from the spirit and scope of the disclosure. The protection scope of the disclosure shall be defined by the appended claims.

What is claimed is:

1. An electronic device, comprising:
   an electromyography value measurement circuit;
   a storage circuit, storing a code;
   an electrode patch; and
   a processor, coupled to the electromyography value measurement circuit, the storage circuit, and the electrode patch, and configured by the code to execute:
   individually applying a corresponding first current to a body part of a user in a plurality of consecutive time intervals through the electrode patch, wherein the plurality of consecutive time intervals comprise an i-th time interval to an (i+N)-th time interval, where i and N are positive integers;
   obtaining a plurality of electromyography values of the body part in each of the plurality of consecutive time intervals through the electromyography value measurement circuit;
   determining a second current corresponding to an (i+N+1)-th time interval based on the first current corresponding to each of the plurality of consecutive time intervals, the body part, at least one personal information of the user, and the electromyography values of each of the plurality of consecutive time intervals, comprising:
   converting the electromyography values in each of the plurality of consecutive time intervals into a first vector;
   converting the first current corresponding to each of the plurality of consecutive time intervals, the body part, and the at least one personal information of the user into a second vector, and splicing the first vector and the second vector into a specific matrix;
   converting the specific matrix into a third vector, and converting the third vector into a reference coefficient; and
   multiplying the reference coefficient by a constant to generate the second current corresponding to the (i+N+1)-th time interval; and
   applying the second current to the body part of the user in the (i+N+1)-th time interval through the electrode patch.

2. The electronic device according to claim 1, wherein the processor is configured to perform:
   obtaining a long short term memory model, wherein the long short term memory model comprises a 1-st hidden layer to an (N+1)-th hidden layer connected in series;
   respectively inputting the individual electromyography values of the i-th time interval to the (i+N)-th time interval into the 1-st hidden layer to the (N+1)-th hidden layer, wherein the long short term memory model generates the first vector in response to the individual electromyography values of the i-th time interval to the (i+N)-th time interval.

3. The electronic device according to claim 1, wherein the processor is configured to perform:
   inputting the first current corresponding to each of the plurality of consecutive time intervals, the body part, and the at least one personal information of the user into a first deep neural network, wherein the first deep neural network generates the second vector in response to the first current corresponding to each of the plurality of consecutive time intervals, the body part, and the at least one personal information of the user.

4. The electronic device according to claim 1, wherein the processor is configured to perform:
   inputting the specific matrix into a second deep neural network, wherein the second deep neural network generates the third vector in response to the specific matrix.

5. The electronic device according to claim 1, wherein the processor is configured to perform:
   converting the third vector into the reference coefficient based on a hyperbolic tangent function, wherein the reference coefficient is between −1 and 1.

6. The electronic device according to claim 1, wherein the processor is further configured to perform:
   obtaining a plurality of electromyography values of the body part in the (i+N+1)-th time interval through the electromyography value measurement circuit;
   determining a third current corresponding to an (i+N+2)-th time interval based on the second current, the body part, the at least one personal information of the user, and the individual electromyography values of the (i+1)-th time interval to the (i+N+1)-th time interval; and
   applying the third current to the body part of the user through the electrode patch in the (i+N+2)-th time interval.

7. The electronic device according to claim 1, wherein before applying the second current to the body part of the user through the electrode patch in the (i+N+1)-th time interval, the processor is further configured to perform:
   obtaining a median frequency value of each of the plurality of consecutive time intervals based on the electromyography values of each of the plurality of consecutive time intervals;
   determining a plurality of frequency value slopes based on the individual median frequency values of an (i+k)-th time interval to the (i+N)-th time interval in the plurality of consecutive time intervals, where k≤N−1; and
   stopping to apply the second current to the body part of the user in response to judging the frequency value slopes as satisfying a first condition or a second condition, otherwise applying the second current to the body part of the user through the electrode patch in the (i+N+1)-th time interval.

8. The electronic device according to claim 7, wherein in response to judging n consecutive frequency value slopes as all positive and individual absolute values thereof as all less than a first preset value, the frequency value slopes are judged as satisfying the first condition, otherwise the frequency value slopes are judged as not satisfying the first condition.

9. The electronic device according to claim 7, wherein in response to judging n consecutive frequency value slopes as all negative or individual absolute values thereof as greater than a second preset value, the frequency value slopes are judged as satisfying the second condition, otherwise the frequency value slopes are judged as not satisfying the second condition.

\* \* \* \* \*